United States Patent
Wedan et al.

(10) Patent No.: US 6,346,080 B1
(45) Date of Patent: Feb. 12, 2002

(54) ENCASEMENT AND TRANSDUCER SHUTTLE ASSEMBLY FOR REMOVABLE IMPLANTED DEVICE

(75) Inventors: Steven R. Wedan, Savage, MN (US); Rebecca M. Johnson, Chassel, MI (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

(21) Appl. No.: 09/432,347

(22) Filed: Nov. 2, 1999

(51) Int. Cl.[7] .................................................. A61B 8/00
(52) U.S. Cl. ......................................................... 600/453
(58) Field of Search ................................. 600/450, 432, 600/453, 455, 458, 467, 488, 454

(56) References Cited

U.S. PATENT DOCUMENTS

| | | | |
|---|---|---|---|
| 5,205,292 A | | 4/1993 | Czar et al. |
| 5,409,009 A | * | 4/1995 | Olson ........................... 600/454 |
| 5,438,997 A | * | 8/1995 | Sieben et al. ................ 600/467 |
| 5,873,835 A | * | 2/1999 | Hastings et al. ............ 600/488 |

* cited by examiner

Primary Examiner—Marvin M. Lateef
Assistant Examiner—Maulin Patel
(74) Attorney, Agent, or Firm—Brown & Michaels, PC (57) ABSTRACT

An implantable and extractable sensor is used for monitoring blood flow and vessel characteristics within a patient. The sensor includes a structurally supportive shuttle that has an angularly offset shelf. A transducer is mounted to this shelf and offset at the same angle so as to utilizes the Doppler effect. Silicone is injection molded around the assembly to provide a housing having a plurality of cutouts that expose portions of release wires running through the housing. The sensor is attached to the vessel by suturing around the exposed portions of the release wires. When the wires are retracted, the sensor can be extracted from the patient without having to reopen the surgical wound. The shuttle provides a consistent location to mount a transducer and also provides the structural support for the silicone housing.

34 Claims, 8 Drawing Sheets

ENCASEMENT AND TRANSDUCER SHUTTLE ASSEMBLY FOR REMOVABLE IMPLANTED DEVICE

BACKGROUND OF THE INVENTION

1. Field of the Invention

This invention relates generally to a removable implanted device that includes a sensor for measuring blood flow and other vessel characteristics. In particular the present invention relates to an encasement and a support structure to house such an implantable device.

2. Description of the Related Art

After certain medical conditions have occurred or certain medical procedures have been performed, it is often desirable to monitor blood flow through various veins or arteries, especially those in close proximity to the heart. For example, monitoring the flow of blood out of a patient's aorta immediately following heart surgery can provide doctors with very valuable information.

Various devices have been designed to obtain blood flow information by making appropriate measurements. One device includes a transducer mounted within a housing. When attached to a blood vessel, the transducer utilizes the Doppler effect to monitor blood flow and the A- or M-mode to monitor the diameter of the vessel. The housing has a plurality of cutouts, with one or more release wires extending through the housing as illustrated in U.S. Pat. No. 5,205,292. The wires are releasably coupled to a front wall of the device and are exposed outside of the housing through the cutouts. These wires allow for the releaseable attachment of the device to a patient's aorta.

A tube is coupled to the proximal end of the housing and extends out of the corpus of the patient. The necessary electrical/data connections made to the device are contained within the tube and provide the appropriate signals to monitoring equipment. The above mentioned release wires also extend through the tube to a point where they are accessible by the surgeon.

In use, the surgeon makes an incision into the patient. The housing of the device is positioned on the appropriate blood vessel, and sutures are used to connect the vessel to the housing via the exposed portions of the release wire. In other words, the exposed portions of the release wire provide anchoring points for the device. With the tube extending out of the corpus, the implantation wound is then sutured. The data lines are connected and patient information is transmitted to the monitoring equipment.

When specific blood flow data is no longer needed, the surgeon locates the portions of the release wires which extend out of the tube and retracts them. This causes a separation of the release wires from the front wall of the housing. As the wires are pulled backwards, they slide through the cutouts, thus releasing the sutures. Once the device is completely free, the surgeon can pull it out of the corpus by retracting the tube. Because the device is so small, it can exit through the opening left for the tube, and hence the surgeon need not create or reopen a wound in order to remove it. This represents a tremendous advantage in patient care, in that the corpus does not have to be needlessly and repeatedly opened to obtain blood flow measurements.

The housing and the transducer must be extremely small in order to be effective. As stated above, the device must unobtrusively sutured to various blood vessels and then removed through a surgical wound. It is critical that the wound remain as small as possible and that it not be unnecessarily disturbed. Obviously, making many of these components as small as possible, while also remaining operable, is often a complicated task. All materials and part configurations need to be optimized so as to meet all of the aforementioned goals. Also, manufacturing challenges need to be accounted for to insure an operating product can be fabricated without incurring exorbitant costs.

In order to be operable and effective, the transducer must be positioned at a specified angle with respect to the major axis of the vessel. Typically, this angle is accomplished by configuring the housing such that a predetermined angle is maintained between the transducer and the bottom of the housing. This is a difficult manufacturing step because the housing is made from compliant silicone. When the transducer is placed into the housing it is difficult to align properly. The most obvious method of fabricating an appropriate housing is to first mold a housing and then have the transducer attached thereto. In the context of this device, this is not an acceptable process as too many variables can be introduced. Specifically, a layer of adhesive is used to attach the transducer. This adhesive introduces a layer of material below the transducer. It is virtually impossible to insure that the layer of adhesive has parallel surfaces, and is free of air bubbles. The presence of either air bubbles or unparallel surfaces can effect the operation of the device.

If the transducer is being attached to a surface of the housing, it is then possible for the surface to be deformed. A deformation in the surface can also adversely effect the operation of the device.

Even if properly aligned, it is difficult to maintain this arrangement as the silicone housing sets. As such, the data obtained may potentially be skewed because of an unnoticed misalignment.

Additionally, the appropriate placement and retention of the release wires creates another manufacturing challenge. As can be appreciated, the release wires must be sufficiently retained within the housing so that suturing will hold the housing in place. Concurrently, the release wires must be sufficiently releaseable so they can be easily withdrawn at an appropriate point in time.

Again, one obvious way of manufacturing a housing which includes these release wires is to take the above discussed preformed housing, drill appropriate passage ways through the housing, and insert the release wires therethrough. However, these drilled holes are typically sized larger than the release wire itself, thus eliminating the natural ability of the housing to retain the release wires. In this configuration, the release wires are thus prone to slide out of the housing when being sutured. If this occurs, the device becomes virtually unusable as the measurements cannot be relied upon.

Another way of manufacturing a housing which includes these release wires is to take the above discussed preformed housing and pierce the release wires through the housing appropriately. This is prone to manufacturing inconsistencies which result in stress or strain on the compliant housing, unequal gripping force by the housing on the wires, ripping of the compliant housing, or improper placement of the wires.

As such, there exits a need to provide an easily removable implant containing a transducer securely and accurately fixed at a predetermined angle with respect to the surface of the implant contacting the wall of the vessel. There also exists a need to provide an implantable device which will maintain and position release wires in a consistent and predictable manner to accommodate appropriate retention of the device while also accommodating desired releaseability.

SUMMARY OF THE INVENTION

The present invention includes a structurally supportive shuttle member having a planar shelf which is offset at a predetermined angle from the main axis of the shuttle. A transducer is then mounted on the shelf, and as such, maintains the same predetermined angle. A cavity exists immediately behind the shelf and opposite the transducer. Acoustical backing material is placed in the cavity to enhance transducer operation. The various electrical components and connections required to operate the transducer are then placed within the space remaining in this cavity, beside the acoustical backing material. Connection to the actual transducer is made via conductive flex tapes which pass through appropriate openings in the shuttle.

Initially, the shuttle assembly will have three struts extending outwardly from its main body segment. The struts are used to provide support alignment and anchoring points for the shuttle during the assembly process. Initially, the transducer is mounted to the shelf and the various electrical connections are made. Next, acoustic backing material is placed in the cavity behind the transducer. The assembly is then insulated with parylene and plated with a gold shield. Release wires are then placed parallel to the major axis of the shuttle and are run through a coil stop that is located adjacent to one end of the shuttle. With all of these components properly in place, the shuttle is ready for encasement.

A housing is injection molded around the shuttle and its attached components. While this molding is used to produce the housing, it is more of an encasement than classical "housing." The housing is formed so as to provide cutouts that provide the necessary suture points. That is, the portions of the release wire exposed through the cutouts accommodate sutures when attached to a patient. Portions of the struts extend out through the housing, and continue to support the assembly until the silicone solidifies. Once the silicone solidifies the extended portions of the struts and one end of the release wires are severed. Lastly, final assembly operations are completed such as placing all associated wiring into a protective tubing. At this point, a properly configured implantable device has been fabricated and is ready to be utilized.

It is an object of the present invention to provide a functioning transducer mounted within a structurally sound housing, wherein an angle of the transducer with respect to a lower wall of the housing is fixed.

It is another object of the present invention to provide a shuttle that can be used during the manufacture of an implanted device which utilizes an ultrasound transducer to measure certain characteristics of the body's function.

It is yet still another object of the present invention to configure the shuttle so that it provides structural support to the housing, once completed.

It is still another object of the present invention to provide an easily manufacturable ultrasound transducer device which includes a shuttle that can support and properly align the components of an implanted device to enhance operation. This includes proper alignment of the transducer itself and appropriate positioning of connections and other acoustic materials. The use of this shuttle also provides for protection of the transducer during manufacturing.

It is yet another object of the present invention which provides for the appropriate retention of release wires to insure they stay in place during suturing, while also easily release when desired.

It is still yet a further object of the present invention to provide an implantable device wherein the electrical and mechanical connections are made without impeding the acoustical performance of the transducer.

It is another object of the present invention to provide a shuttle assembly for an implantable device wherein the shuttle includes a cavity for containing acoustical backing material to further enhance the operation of a transducer.

It is still another object of the present invention to electrically shield the components at an implantable device so that patient safety is assured and so that the components function properly.

It is a further object of the present invention to encase the electrically shielded components of an implantable device in a silicone housing.

DETAILED DESCRIPTION OF THE PREFERRED EMBODIMENT

Figure 1:
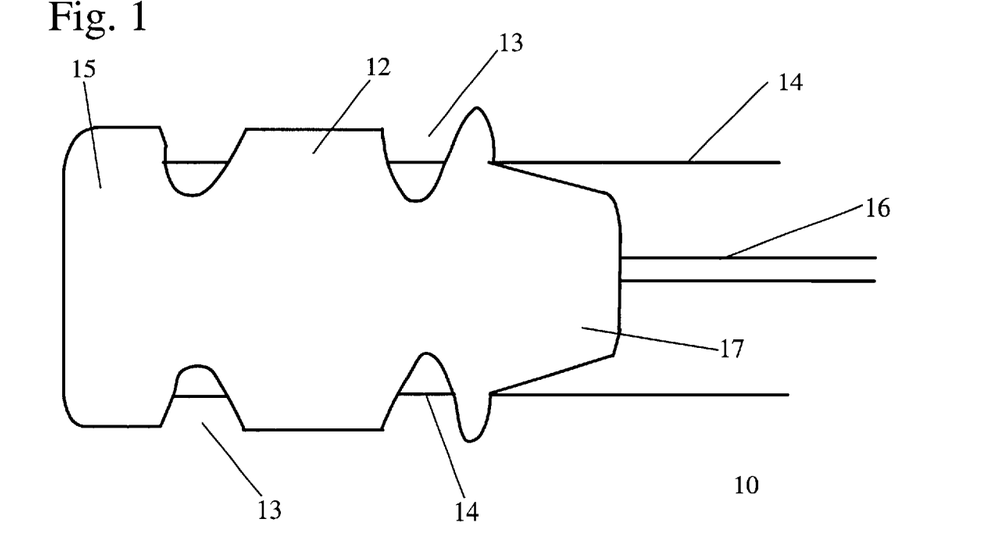
FIG. 1 is a top, planar view of a completed housing for an implanted device with the release wires extending through cutouts in the housing and trailing from the proximal end of the housing.
Figure 2:
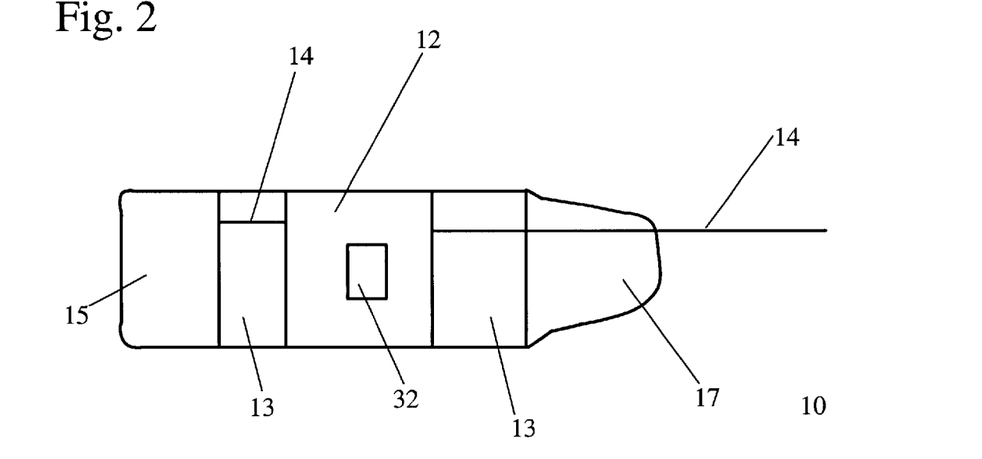
FIG. 2 is side planar view of a completed housing for an implanted device.

Referring to FIGS. 1 and 2, a substantially complete implantable sensor head is illustrated and generally referred to as 10. Sensor head 10 has a contoured housing 12 that is formed from an injection molding process. Preferably, silicone is used to form housing 12, as silicone is structurally reliable and medically safe for implantation procedures. Furthermore, the implant utilizes an acoustic transducer and silicone has excellent acoustic properties. Housing 12 has a number of arcuate cutouts 13 spaced along its outer perimeter. A pair of release wires 14 are shown to extend through housing 12, and are partially exposed as they pass through each of the cutouts 13. The release wires 14 are releasably secured within housing 12 by the frictional engagement of the silicone. Release wires 14 exit the proximal end 17 of housing 12 and extend to a release mechanism (not shown). Similarly, electrical wires 16 exit proximal end 17 and are coupleable to appropriate monitoring equipment (again, not shown).

As will later be explained in greater detail, sensor head 10 is a sensor or probe used to measure fluid flow. Housing 12 encases an ultrasound transducer that sends and receives signals. The transducer is preferably ultrasonic and is mounted onto a shuttle assembly, which is also encased within housing 12.

Figure 3:
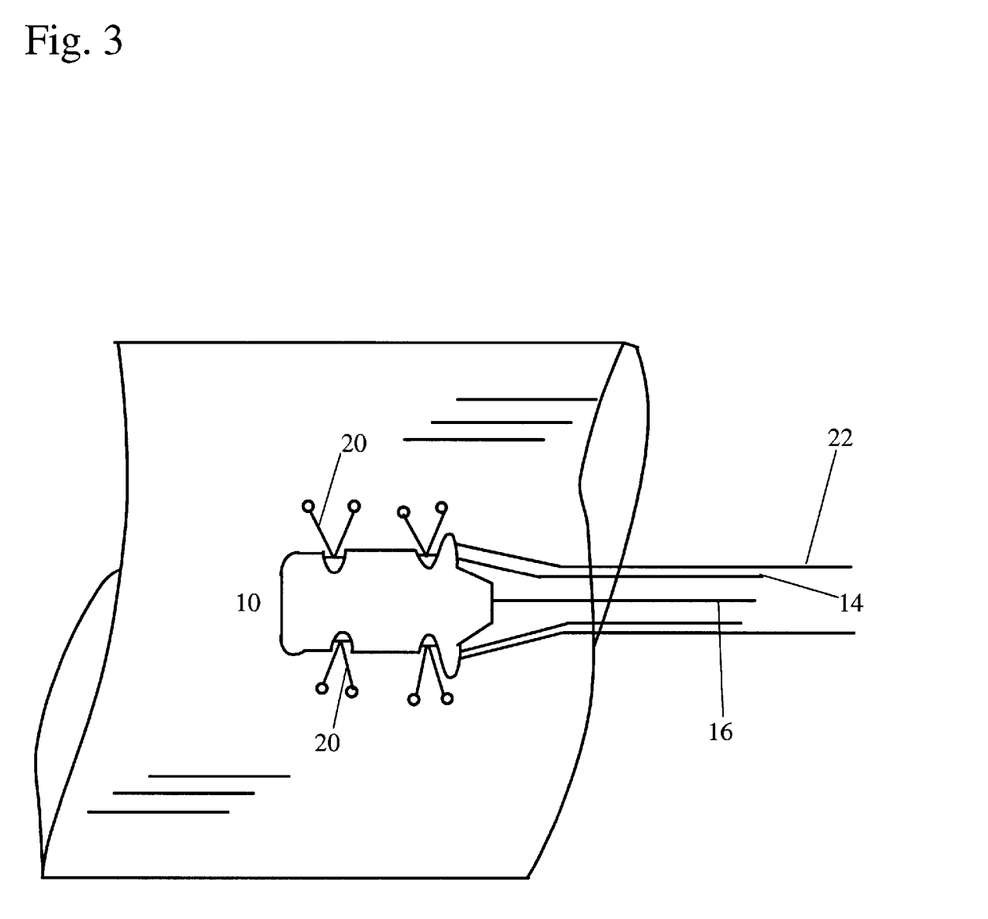
FIG. 3 is a top view of a completed housing attached to a vessel, by having the exposed portions of the release wires sutured to the wall of the vessel.

FIG. 3 illustrates sensor head 10 as it is attached to an artery 18. Sutures 20 are wrapped about the portions of release wires 14 that are exposed at cutouts 13 and are attached to the wall of artery 18. Tubing 22 is coupled to the proximal end 17 of housing 12 and encases the extending portions of release wires 14 and electrical wires 16. After implantation, the tubing extends out of the corpus of the patient. While in use, the electrical wires 16 are coupled to various types of monitoring equipment. The transducer operates to obtain various measurements, including blood flow and arterial dimensions. When monitoring is no longer needed, the surgeon pulls release wires 14, dislodging them from their encasement in the walls of housing 12 and retracts them out through tubing 22. Release wires 14 can be fully retracted but must at least be retracted beyond the cutouts 13. Once release wires 14 are retracted beyond cutouts 13, the sutures 20 no longer bind housing 12 to artery 18. As such, the surgeon can then extract sensor head 10 from the patient by retracting tubing 22. The sutures 20 will harmlessly remain in the patient or dissolve over time.

As previously mentioned, the sensor head 10 utilizes an ultrasonic transducer to perform appropriate monitoring. Appropriate alignment and handling of this sensor is critical to insure proper operation. As can be appreciated, this makes fabrication very complicated. Further, issues of appropriate electrical connections and shielding all further complicate the fabrication process. Consequently, a internal structure for sensor head 10 must be carefully designed to allow for easy fabrication.

Referring to FIGS. 4–7, a shuttle 24 forms the foundation for the assembly of components into the sensor head 10. Shuttle 24 is a solid and rigid mechanical structure having a medially disposed main body 26. Shuttle 24 can be made from any suitable material such as polycarbonate. A distal tee 28 and a proximal tee 30 extend from main body 26. Right strut 32, left strut 34, and tail strut 36 also extend away from the main body 26.

Figure 4:
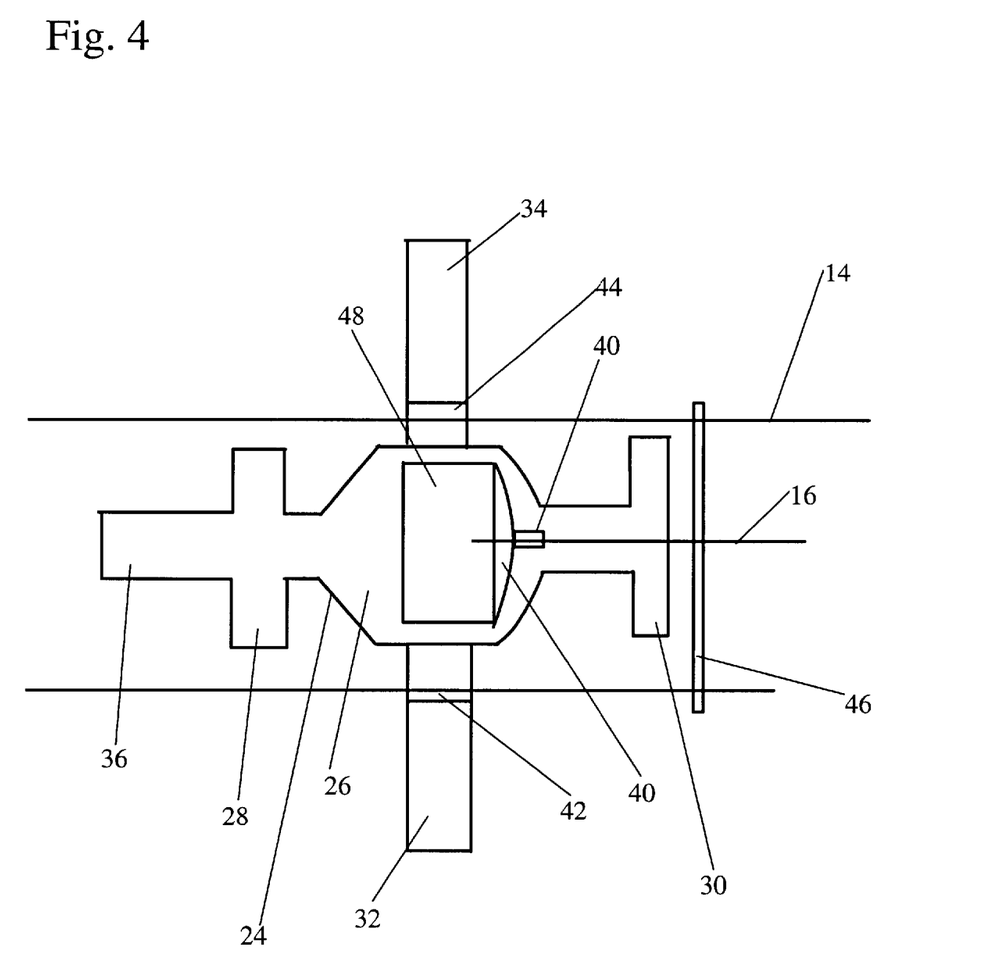
FIG. 4 is a top planar view of a shuttle assembly, prior to injection molding, with the release wires and coil stop properly positioned.
Figure 6:
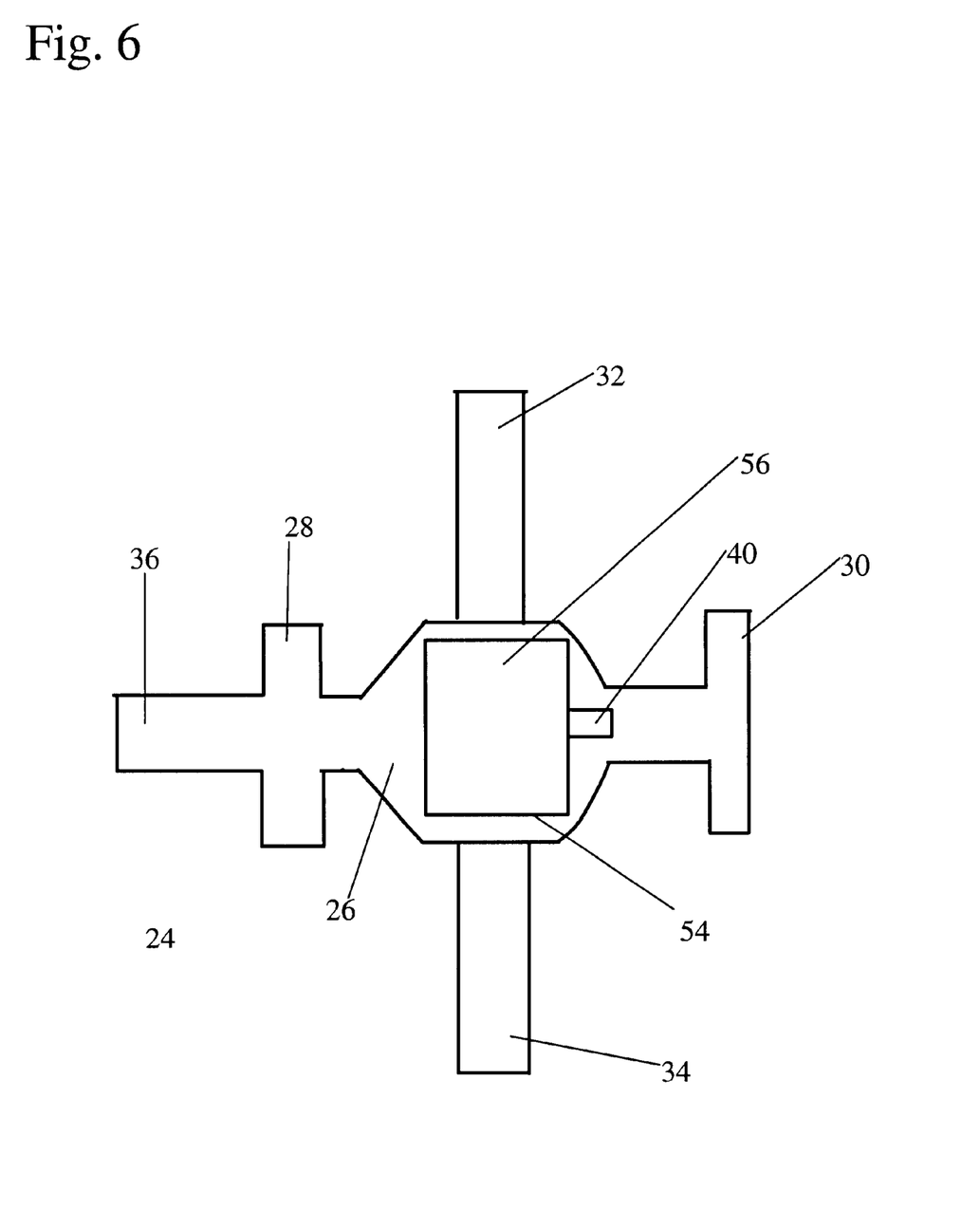
FIG. 6 is a bottom, planar view of the shuttle assembly.
Figure 7:
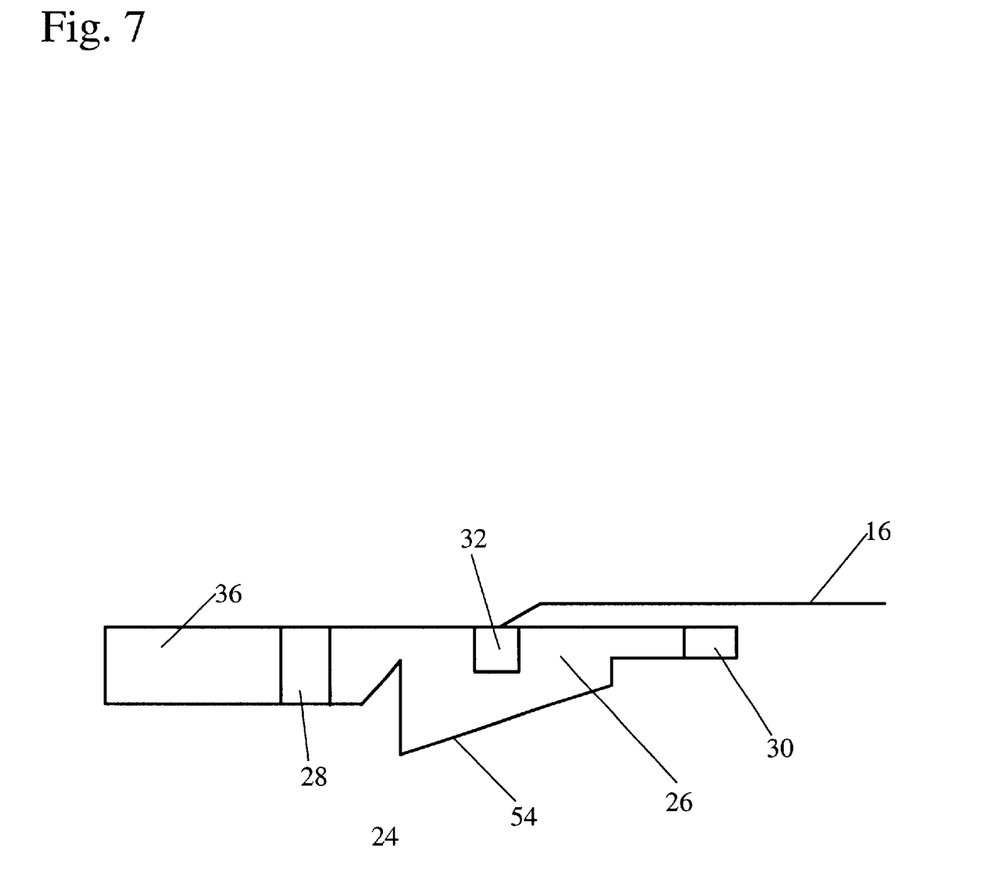
FIG. 7 is a side, planar view of the shuttle assembly.

Main body 26 includes a cavity 38 with a slanted shelf 54 disposed forming bottom of the cavity 38. A slot 40 is provided which connects the shelf 54 to the remainder of cavity 54. Slanted shelf 54 is specifically configured at a predetermined angle with respect to the main body 26 of shuttle 24. The molding process used to fabricate shuttle 24 provides for tight control of this angle, thus insuring a repeatable configuration for shelf 54.

Figure 8:
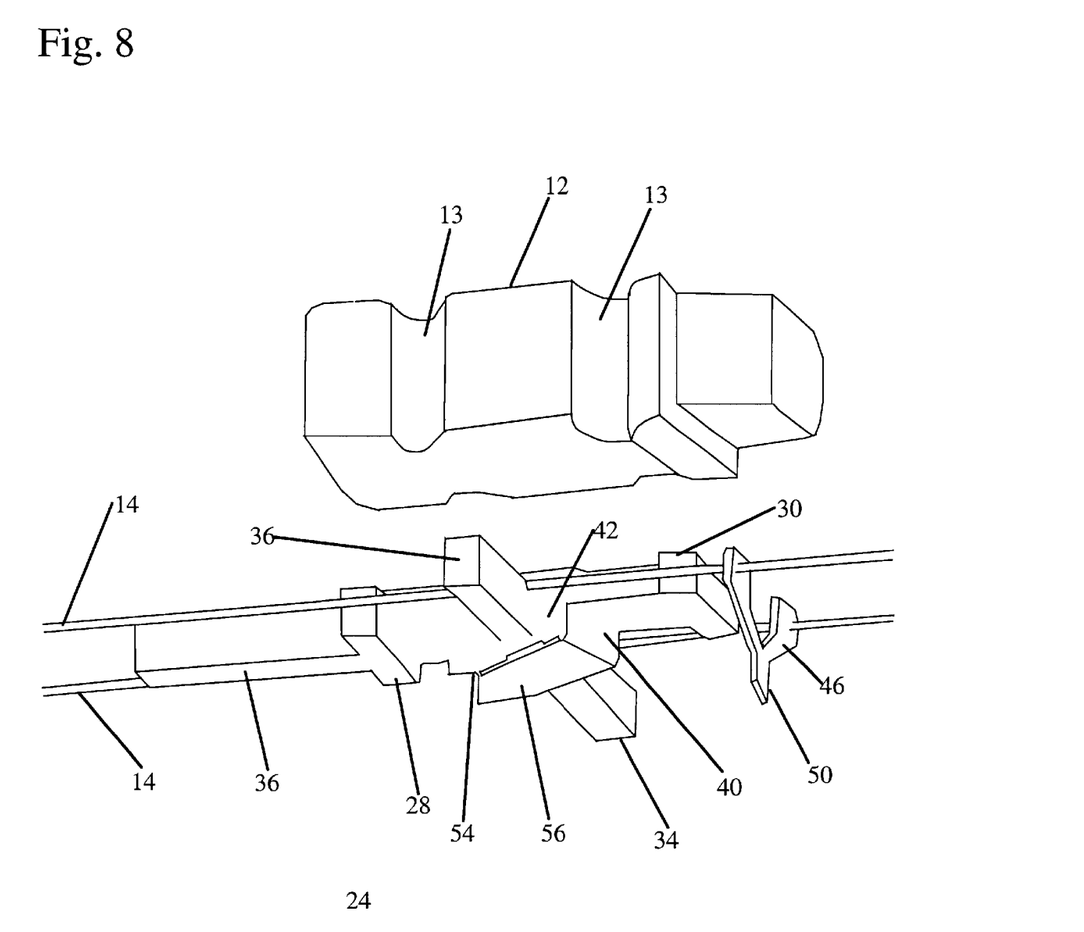
FIG. 8 is a lower perspective view of the shuttle assembly in relation to the silicone housing which will be later be formed around the shuttle assembly.

As seen in FIG. 8, a transducer 56 is coupled to the shelf 54 and assumes the same angle with respect to main body 26. In order to utilize the Doppler effect to obtain measurements, the transducer 56 must be angled with respect to the artery 18 wall. The use of shelf 54 as a mounting structure provides a convenient and consistent way to precisely control this angle in sensor head 10.

Flexible contacts (not shown) are flushly coupled to each major face of the transducer 56 providing the appropriate connections. These flexible contacts can then be connected with additional circuitry to provide efficient transducer operation. By connecting in this way, the attachment of the contacts will not acoustically interfere with the transducer.

Acoustic backing material 48 is placed within cavity 38, leaving enough room within cavity 38 for any electrical connections or components (including the flex contacts) necessary to operate transducer 56. The acoustic backing material 48 is provided to increase the sensitivity of the transducer 56 and to accommodate broadband operation (i.e., having a short ring-down time). It is advantageous to utilize the acoustic backing material because it has an impedance close to that of air, but also provides a mechanical damping effect. It is a soft material, making it easier to work with, yet still having a very high attenuation.

Electrical wires 16, coupled to transducer 56 through the flexible contacts extend towards and beyond proximal tee 30. Various notches and grooves can be cut into shuttle 24 to direct and retain the various electrical wires. The shuttle 24, transducer 56, and all of the electrical contacts and components are coated with a layer of parylene which acts as an electrical insulator. Alternatively, any other acoustically transparent conformal coating could be used. The shuttle 24 is also plated with gold (or any other appropriate metal) to shield the transducer, minimizing its susceptibility to noise and electromagnetic emissions. A shield wire is attached (shown as part of electrical wire 16) to maintain appropriate contact with the shield.

Figure 5:
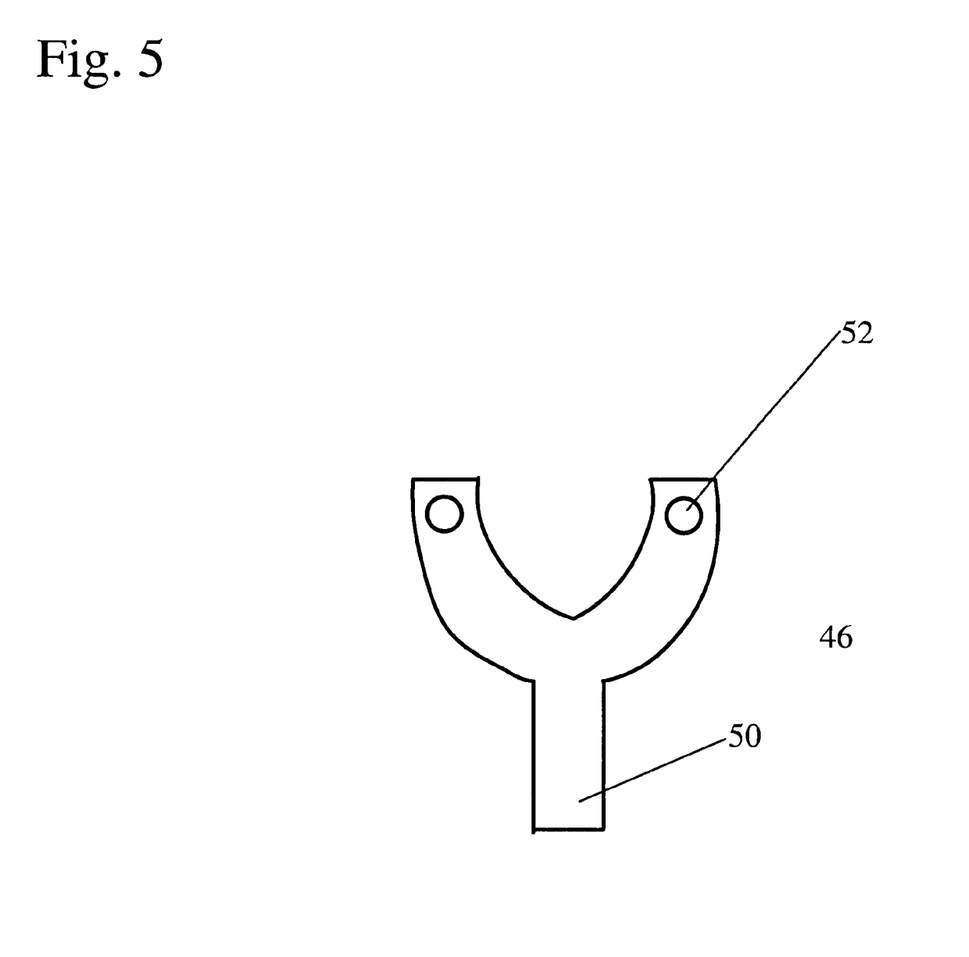
FIG. 5 is a front, planar view of a coil stop.

Right strut 32 and left strut 34 are provided with right notch 42 and left notch 44, respectively. To encase transducer 56 and all other components, shuttle 24 is positioned in an injection molding device (not shown) such that is supported by the three struts 32, 34, 36, leaving the remainder of the shuttle 24 and its attached components entirely unencumbered. Release wires 14 are coated with parylene and then placed parallel to a main axis of shuttle 24. The release wires 14 are sufficiently rigid to facilitate this arrangement. The release wires 14 pass through right and left notches 42,44 so that they are in close proximity to main body 26. Care must be taken so that the release wires 14 do not contact the gold plated shuttle 24, as this represents a potential risk to the patient's safety. A yoke shaped coil stop 46 is positioned near proximal tee 30 and the release wires 14 extend through wire release holes 52, thus supporting coil stop 46 in the position illustrated.

Once the arrangement of FIG. 4 is achieved and the components are in place, silicone is injected into a mold surrounding these elements, thus forming contoured housing 12. The contoured housing provides a structured encasement for shuttle 24 and all related components. Most significantly, this provides an encasement for transducer 56 which is conducive to transmitting sound to/from the patient's tissue. Further, because the shuttle can be easily aligned during this molding operation, the alignment of transducer 56 with respect to the bottom surface of housing 12 can be carefully controlled. As previously mentioned, sensor head 10 is sutured to an artery in order to perform its intended monitoring. In this arrangement, the bottom surface of sensor head 10 is placed in direct contact with the artery surface. Due to the controlled alignment between transducer 56 and the bottom surface of sensor head 10, a controlled angle is also provided when sensor 10 is attached to the patient's artery.

The cutouts 13 are located so that release wires 14 are partially exposed, and a gap is provided between the exposed portion and the remainder of housing 12. The shape of the cutouts 13 is significant. In previous removable implantable devices, the cutouts have been relatively long, large radiused, arcuate configurations. As such, relative little force was required to cause the release wires to bend or arch away from the housing. When the sutures were placed around the release wires, they could be pulled away from the housing. In order to prevent the wires from being pulled out of the housing by the tension generated by the sutures, a relatively firm clamping mechanism had to be placed into the housing that rigidly and securely held the release wires in place. Hence, upon removal, a large amount of force had to be applied to release the wire, which necessitated the use of coil stop 46. In the present invention, the cutouts 13 are relatively short and provide a nearly perpendicular plane to the entrance and exit of the release wires 14. Hence, much more force would have to be applied to cause the release wires 14 to arch away from the housing. This is because only a short segment of the wire is exposed and it passes through walls that are perpendicularly offset from it. As such, the suturing process will not flex the wires 14. Therefore, less force is required to retract the wires 14. Since less force is required, the silicone encasement of the wires 14 is sufficient to hold them in place. Furthermore, the restriction forces are minimal, hence it is very unlikely that the coils (not shown) would be forced into housing 12 (and blocking cutout 13). Therefore, coil stop 46 is now optional.

The coil stop 46 (when used) is put in place so that when the release wires 14 are retracted, the coils (not shown) do not enter the silicone housing 12 and obstruct the cut outs 13. Were this to happen, the surgeon would not be able to retract the implant and would have to reenter the corpus. Each release wire 14 is held in place due to the frictional engagement of the silicone that surrounds it. In addition, each wire 14 has a pair of metal coils surrounding the wire 14 outside of but proximate to the housing 12. The surgeon manipulates the wires 14 and coils so that the coils move towards the housing 12, causing the wires to move away from (out of) housing 12. The parylene coated release wires 14 are fairly easy to extract from the silicone. As such, the coil stop 46 is optional and is only necessary if it is expected that the separation of the wires 14 from the housing 12 will be made more difficult.

Figure 9:
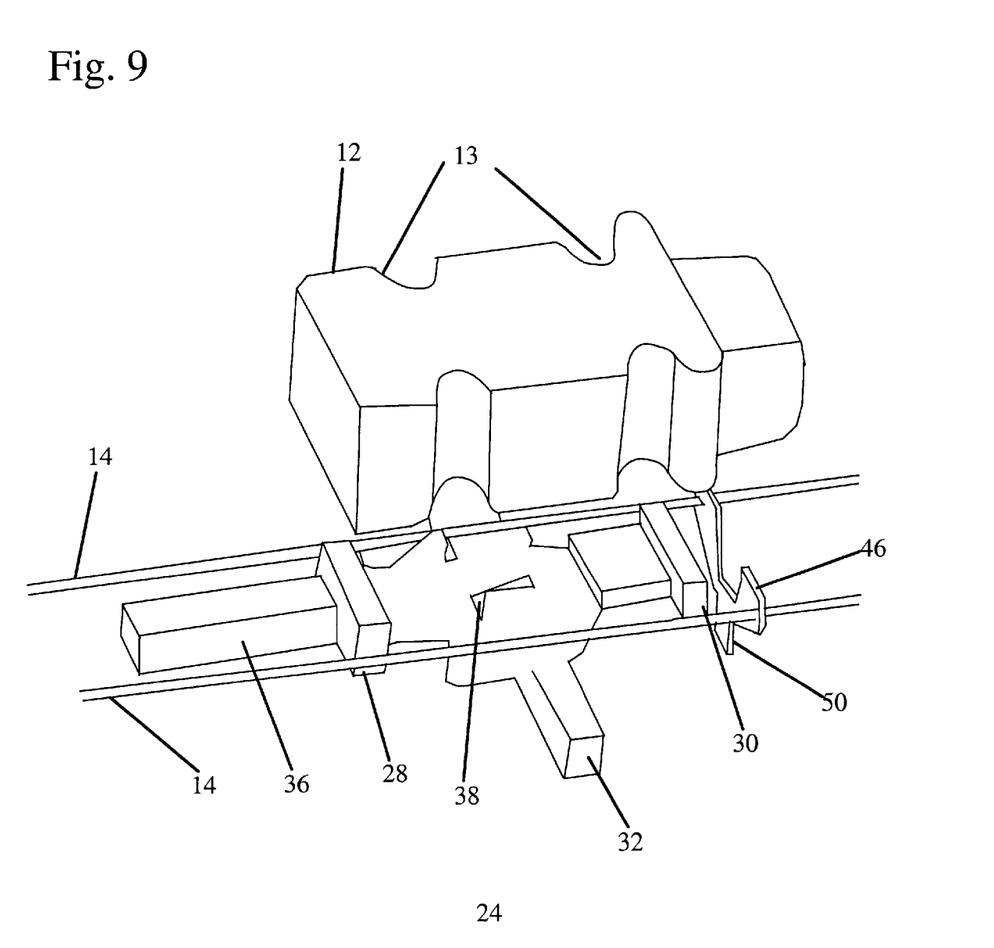
FIG. 9 is an upper perspective view of a shuttle assembly in relation to the silicone housing which will be later be formed around the shuttle assembly.

FIGS. 8 and 9 illustrate a comparison between the shuttle 24 (and its attached components) prior to injection molding and the formed silicone portion of housing 12. As shown, various elements will extend beyond the housing 12, once the silicone is molded. For example, release wires 14 will extend in both a proximal and distal direction beyond housing 12. Furthermore, right, left, and tail struts 32, 34, 36 will extend beyond housing 12. Once the silicone has hardened, the extended portions of struts 32, 34, 36 are trimmed away flush with housing 12. The release wires 14 may simply be cut to terminate in the silicone housing 12, with the silicone providing a sufficient clamping action on the wires 14 to hold them in place, until they are forcibly pulled from the silicone. Another alternative is to use a single release wire 14 that it is looped through the distal end 15 of the housing 12, with each of the ends of wire 14 then extending outside of the patient, where they are secured. Instead of releasing from the silicone housing or a release mechanism, the looped wire is simply disconnected outside of the patient, and then one end is pulled, until the sutures 20 are free. The tab 50 of coil stop 46 is also trimmed away.

Since silicone is generally pliable, the remaining portion of shuttle 24 provides most of the structural support for the sensor head 10. The distal and proximal tees 28, 30 are embedded within the silicone and form a "hammerhead" structure that increases the overall structural integrity of the device. The angled portion of main body 26 provides depth to the shuttle 26, further increasing its rigidity. Finally, the untrimmed portions of right and left struts 32 and 40 that remain within housing 12 form a "medial tee" and offer additional rigidity. The shuttle 24 provides an optimal balance between providing sufficient rigidity, while ensuring that the shuttle assembly is fully encased.

As shown, the bottom surface of housing 12, which contacts the wall of the artery is slightly convex. When applied to the convex wall of an artery, the housing 12 causes the artery to become partially concave to receive the housing 12. As such, this contact will force any air trapped between the housing 12 and the artery outward, thus assuring flush contact. Also, this will eliminate air bubbles, which can detrimentally effect the operation of the device.

To complete the implant, a sufficient length of the release wires 14 and electrical wires 16 are inserted into a similar length of tubing 22. An end of the tubing 22 is then coupled to the proximal end of housing 12, forming a completed sensor head 10 as shown in FIGS. 1–3.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. An implantable, extractable sensor, comprising:
    a shuttle having main body including a shelf being angularly offset from a major axis of the main body;
    a transducer mountable to the shelf; and
    a housing encasing the shuttle and the transducer, the housing having at bottom surface substatially parallel with the major axis of the main body.

2. The sensor of claim 1 further comprising a release mechanism removably attached to the housing, the release mechanism including a suture contact loop for attaching sutures to the housing.

3. The sensor of claim 1 wherein the release mechanism includes a pair of release wires removably encased by the housing, the release wires extending through a pair of recesses in the housing to form an enclosed suture opening which is surrounded by the housing and the release wires.

4. The sensor of claim 1 wherein the shuttle has a cavity situated behind the shelf and opposite the transducer, wherein the cavity is filled with acoustic backing material.

5. The sensor of claim 1 wherein the shuttle further includes an alignment structure which has a known orientation with respect to the shelf.

6. The sensor of claim 5 wherein the alignment structure includes a first strut member extending from the main body, perpendicular to the major axis and a second strut member extending from the main body, opposite from the first strut member and perpendicular to the major axis.

7. The sensor of claim 6 wherein the alignment structure further includes a tail strut axial aligned with the major axis and extending from the distal end of the shuttle.

8. The sensor of claim 1 wherein the transducer is an ultrasonic transducer.

9. The sensor of claim 8 wherein the angular offset is chosen to allow the transducer to utilize the Doppler effect.

10. The sensor of claim 1, further including a coil stop encased within the housing, wherein the release wire is passed through a hole in the coil stop.

11. The sensor of claim 1 wherein the housing is silicone.

12. The sensor of claim 1 wherein a parylene coating covers the shuttle and the transducer.

13. The sensor of claim 12 wherein gold plating covers the parylene coated shuttle and transducer.

14. The sensor of claim 1 wherein gold plating covers the shuttle and transducer.

15. The sensor of claim 1 wherein the cutout includes two walls, wherein the release wire passes through each wall and the release wire approximately perpendicular to the two walls.

16. A method of making an implantable, extractable sensor, comprising:

providing a shuttle having a main body and a cavity disposed within the main body, with a shelf provided within the cavity, the shelf being angularly offset from a major axis of the main body, the shuttle further including at least one strut which extends outwardly from the main body;

mounting a transducer on the shelf;

supporting the shuttle by engaging the strut, leaving the remainder of the shuttle unencumbered;

placing a release wire in close proximity to the main body and parallel to the major axis; and encasing the shuttle, the transducer and a portion of the release wire in a housing that has at least one cutout, wherein the cutout exposes a section of the release wire.

17. The method of claim 16 firther comprising:

trimming any portion of the strut which extends beyond the housing; and trimming any excess portion of the release wire.

18. The method of claim 16 wherein the shuttle also includes a proximal tee and a distal tee to provide structural support within the housing.

19. The method of claim 16, further comprising:

placing acoustical backing material in a portion of the cavity.

20. The method of claim 16 wherein three struts are provided so that the shuttle is securely supportable.

21. The method of claim 20 further comprising:

trimming portions of the struts that extend beyond the housing.

22. The method of claim 16 wherein the transducer is ultrasonic.

23. The method of claim 16 wherein a plurality of release wires are provided.

24. The method of claim 23, further comprising:

placing a coil stop in proximity to the shuttle; and running the release wires through holes in the coil stop.

25. The method of claim 16 wherein the strut includes a notch and the release wire passes through the notch.

26. The method of claim 16 wherein encasing includes injecting a liquefied material into a mold surrounding the shuttle.

27. The method of claim 26 wherein the material is silicone.

28. The method of claim 16, further including:

coupling the release wire to a portion of the housing so that the release wire can be selectively withdrawn.

29. The method of claim 16, further comprising:

coating the shuttle and the transducer with an electrical insulator.

30. The method of claim 29 wherein the electrical insulator is parylene.

31. The method of claim 30 further including:

plating the shuttle and the transducer with gold.

32. The method of claim 31, further including:

spacing the release wire away from the gold plating so that the release wire does not contact the gold plating.

33. The method of claim 29 further including:

plating the shuttle and the transducer with gold.

34. The method of claim 33, further including:

spacing the release wire away from the gold plating so that the release wire does not contact the gold plating.

* * * * *